(12) United States Patent
Hamano et al.

(10) Patent No.: US 10,365,151 B2
(45) Date of Patent: Jul. 30, 2019

(54) INSPECTION PROBE

(71) Applicant: IHI CORPORATION, Tokyo (JP)

(72) Inventors: Toshiaki Hamano, Tokyo (JP); Eisuke Shiina, Tokyo (JP)

(73) Assignee: IHI CORPORATION, Tokyo (JP)

( * ) Notice: Subject to any disclaimer, the term of this patent is extended or adjusted under 35 U.S.C. 154(b) by 162 days.

(21) Appl. No.: 15/491,318

(22) Filed: Apr. 19, 2017

(65) Prior Publication Data

US 2017/0219422 A1    Aug. 3, 2017

Related U.S. Application Data

(63) Continuation of application No. PCT/JP2014/083553, filed on Dec. 18, 2014.

(51) Int. Cl.
*G01V 8/10* (2006.01)
*G01N 29/04* (2006.01)
(Continued)

(52) U.S. Cl.
CPC ............. *G01H 9/008* (2013.01); *G01N 29/04* (2013.01); *G01N 29/2468* (2013.01);
(Continued)

(58) Field of Classification Search
CPC .... G01H 9/008; G01N 29/04; G01N 29/2487; G01N 29/265; G01N 29/2468;
(Continued)

(56) References Cited

U.S. PATENT DOCUMENTS

2012/0181434 A1* 7/2012 Sawada ................. G01T 1/2002
250/361 R
2015/0054942 A1* 2/2015 Coombs ................. G01N 29/24
348/125
(Continued)

FOREIGN PATENT DOCUMENTS

JP    61-200463 A    9/1986
JP    06/018247 A    1/1994
(Continued)

OTHER PUBLICATIONS

Taiwan Office Action with English concise explanation, Taiwan Patent Application No. 103144265, dated Dec. 4, 2015, 6 pgs.

*Primary Examiner* — Jacques M Saint Surin
(74) *Attorney, Agent, or Firm* — Volpe and Koenig, P.C.

(57) ABSTRACT

Disclosed is an inspection probe of an inspection system that includes an ultrasonic probe that is freely movable on a test object and irradiates the test object with an ultrasonic wave to detect a reflected wave, and a calculation unit that executes arithmetic processing according to a detection result according to the ultrasonic probe to acquire a flaw detection result of the test object. The inspection probe includes a chassis that is freely movable on a sheet material where a two-dimensional pattern disposed on the test object and indicating a position on the test object is drawn. The ultrasonic probe is fixed to the chassis so that an incident point of an ultrasonic wave that is incident onto an opposing surface of the test object from the ultrasonic probe is within an angle of view of the reader which reads the two-dimensional pattern.

5 Claims, 6 Drawing Sheets

(51) Int. Cl.
  *G01N 29/24* (2006.01)
  *G01N 29/265* (2006.01)
  *G01H 9/00* (2006.01)

(52) U.S. Cl.
  CPC ....... *G01N 29/2487* (2013.01); *G01N 29/265* (2013.01); *G01V 8/10* (2013.01); *G01N 2291/044* (2013.01); *G01N 2291/056* (2013.01); *G01N 2291/267* (2013.01); *G01N 2291/2634* (2013.01)

(58) Field of Classification Search
  CPC ..... G01N 2291/2634; G01N 2291/267; G01N 2291/044; G01V 8/10
  USPC .......................................................... 73/622
  See application file for complete search history.

(56) References Cited

U.S. PATENT DOCUMENTS

2015/0135799 A1* 5/2015 Yamano ................. G01N 29/30
  73/1.82
2015/0219602 A1* 8/2015 Bond-Thorley ..... G01N 29/221
  73/632

FOREIGN PATENT DOCUMENTS

| JP | 2001-349878 A | 12/2001 |
|----|---------------|---------|
| JP | 2006-170766 A | 6/2006 |
| JP | 2008-089317 A | 4/2008 |
| JP | 2010-054497 A | 3/2010 |
| JP | 2010-096520 A | 4/2010 |
| TW | M296370 | 8/2006 |
| TW | M406734 U1 | 7/2011 |

* cited by examiner

SCANNING DIRECTION

← SCANNING DIRECTION

INSPECTION PROBE

CROSS-REFERENCE TO RELATED APPLICATION

This application is a continuation application based on PCT Patent Application No. PCT/JP2014/083553, filed on Dec. 18, 2014. The content of the PCT Patent Application is incorporated herein by reference.

The present disclosure relates to an inspection probe that includes an ultrasonic probe.

DESCRIPTION OF RELATED ART

Japanese Patent Application No. 2001-349878 discloses an ultrasonic probe capable of correctly acquiring position data on a test object. The ultrasonic probe includes a vibrator that transmits and receives an ultrasonic wave to and from the test object, an optical position detector that includes an optical sensor that reads a pattern on an opposing surface of the test object at a predetermined cycle and detects a current position thereof on the test object according to the amount of movement of a pattern read at an arbitrary cycle by the optical sensor from the same pattern read at an immediately previous cycle, and a chassis that accommodates the vibrator and the optical position detector.

SUMMARY

According to the ultrasonic probe in the related art technique described above, when the pattern on the opposing surface of the test object is accurately read by the optical sensor and the position of the ultrasonic probe is detected by the optical position detector according to the accurately read pattern, the reading of the pattern may be continuously performed without noticing that air bubbles are inserted between the pattern on the opposing surface of the test object and the optical sensor, or the reading of the pattern by the optical sensor may be hindered by reflected light from the opposing surface of the test object, which may hinder accurate reading of the pattern.

In order to solve the above problem, an object of the disclosure is to provide a technique capable of preventing reading of a pattern using an optical sensor from being hindered by light reflected from an opposing surface of a test object and easily confirming whether air bubbles are inserted between the pattern on the opposing surface of the test object and the optical sensor to read the pattern on the opposing surface of the test object with high accuracy.

According to the first aspect of the disclosure, there is provided an inspection probe of an inspection system that includes an ultrasonic probe that is freely movable on a test object and irradiates the test object with an ultrasonic wave to detect a reflected wave, and a calculation unit that executes arithmetic processing according to a detection result according to the ultrasonic probe to acquire a flaw detection result of the test object, the inspection probe including: a chassis that is freely movable on a sheet material where a two-dimensional pattern disposed on the test object and indicating a position on the test object is drawn and has transparency and sonic wave permeability; the ultrasonic probe that is fixed to the chassis; a reader that is fixed to the chassis and reads the two-dimensional pattern, the reader having a predetermined angle of view; and an illumination that is fixed to the chassis, in which the ultrasonic probe is fixed to the chassis so that an incident point of an ultrasonic wave that is incident onto an opposing surface of the test object from the ultrasonic probe is within the angle of view of the reader.

According to the disclosure, it is possible to prevent reading of a pattern using an optical sensor from being hindered by reflected light from an opposing surface of a test object. Further, it is possible to easily confirm whether air bubbles are inserted between the pattern on the opposing surface of the test object and the optical sensor. Thus, it is possible to accurately read the pattern on the opposing surface of the test object, and thus, it is possible to prevent the pattern from being continuously read although sonic waves are not incident due to insertion of air bubbles.

DETAILED DESCRIPTION

Figure 1:
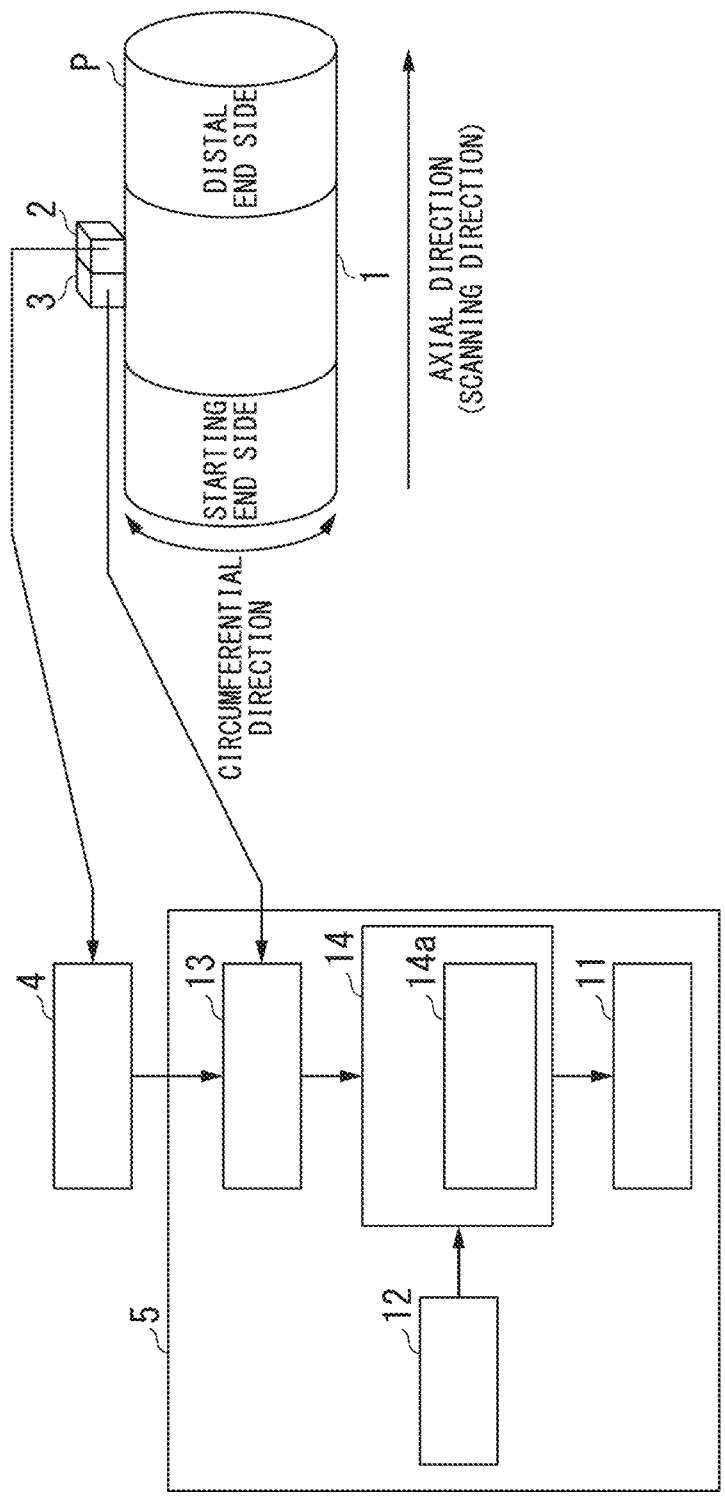
FIG. 1 is a functional block diagram of an inspection system according to a first embodiment of the disclosure.

First, a first embodiment of the disclosure will be described. An inspection system that includes an ultrasonic probe 2 according to the first embodiment of the disclosure is used for inspection of a pipe P which is an example of a test object, and detects cracks or the like generated in a weld line of the pipe P. The inspection system includes a sheet material 1, an ultrasonic probe 2, a reader 3, an ultrasonic flaw detector 4, and a calculation unit 5, as shown in FIG. 1.

Figure 2:
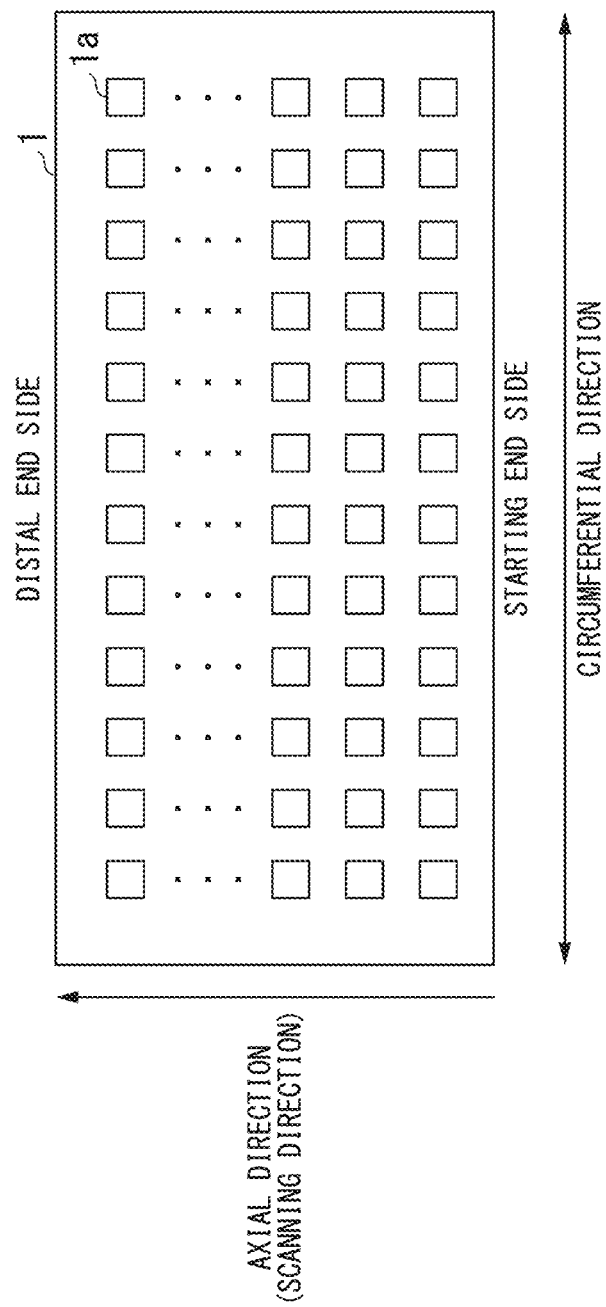
FIG. 2 is a diagram schematically showing a surface of a sheet material in the first embodiment of the disclosure.

As shown in FIG. 1, the sheet material 1 is attached to a surface of the pipe P. As shown in FIG. 2, on the surface of the sheet material 1, QR codes (registered trademark) 1a (two-dimensional pattern) are drawn on the sheet material 1 in an axial direction and a circumferential direction on the pipe P. Data indicating a position (coordinates) on the pipe is encrypted in the QR code 1a. The QR codes 1a are disposed at an interval of 10 mm in the axial direction and the circumferential direction of the pipe P, for example. Further, the sheet material 1 is not in direct contact with the surface of the pipe P, but is attached thereto with the surface of the pipe P being coated with glycerin paste (contact medium) that propagates an ultrasonic wave. In this way, since the sheet material 1 is attached through the glycerin paste coated on the pipe P, the sheet material 1 may come in close contact with the pipe P due to the viscosity of the glycerin paste, and even when irregularities are present on the surface of the pipe P, it is possible to attach the sheet material 1 to be flat.

The ultrasonic probe 2 is connected to the ultrasonic flaw detector 4 through a coaxial cable, and is able to move on the pipe P. Further, the ultrasonic probe 2 generates an ultrasonic wave from a distal end, detects a reflected wave of the ultrasonic wave, and outputs the detection result to the ultrasonic flaw detector 4 as a detection signal. For example, the ultrasonic probe 2 scans the surface of the pipe P manually by an inspector, and detects a reflected wave of an ultrasonic wave, indicating cracks or the like of the pipe P.

As the ultrasonic probe 2, a single vibrator may be used, or a vibrator array in which vibrators are arranged in an array may be used.

The reader 3 is an optical reader having a predetermined angle of view y, which is attached in the vicinity of the ultrasonic probe 2 and reads the QR code 1a on the surface of the sheet material 1 attached to the pipe P. The reader 3 is connected to a communication I/F unit 13 through a signal cable, and outputs an image signal in which an image of the read QR code 1a is included to the communication I/F unit 13. For example, the reader 3 includes a light emitting unit that includes a light emitting element such as a light emitting diode (LED), and an imaging unit such as a charge coupled device (CCD) camera, and is mounted on a front side or a rear side in a movement direction (scanning direction) of the ultrasonic probe 2.

Further, in this embodiment, the reader 3 is integrated with the ultrasonic probe 2 by being fixed to a common chassis 10 (which will be described later).

The ultrasonic flaw detector 4 is connected to the ultrasonic probe 2, and is also connected to the communication I/F unit 13 of the calculation unit 5. The ultrasonic flaw detector 4 supplies power to the ultrasonic probe 2 and the reader 3, performs A/D-conversion on a detection signal input from the ultrasonic probe 2, and outputs the converted signal to the communication I/F unit 13 of the calculation unit 5.

A direction of an arrow in FIG. 1 indicates a signal advancing direction, and is not associated with a direction of the above-described power supply.

Further, the ultrasonic probe 2 may be supplied with power from the ultrasonic flaw detector 4, and the reader 3 may be supplied with power from the communication I/F unit 13.

The connection of the ultrasonic probe 2 and the reader 3 is not limited to wired connection, and may be wireless connection.

In addition, a plurality of ultrasonic probes 2 may be provided.

The calculation unit 5 is a personal computer of a desk-top type, a notebook type, or the like, connected to the ultrasonic flaw detector 4, for example, and as shown in FIG. 1, includes a display unit 11, an operation unit 12, the communication I/F unit 13, and a calculation control unit 14.

The display unit 11 is a display such as a cathode ray tube (CRT) display or a liquid crystal display, and displays various screens under the control of the calculation control unit 14.

The operation unit 12 includes a pointing device such as a mouse, and a keyboard, and outputs an operation instruction received from a user to the calculation control unit 14.

The communication I/F unit 13 performs transmission and reception of various signals with the ultrasonic flaw detector 4 through a communication cable under the control of the calculation control unit 14.

The communication I/F unit 13 is further connected to the reader 3 through a signal cable, and receives an image signal of the QR code 1a read by the reader 3. The communication I/F unit 13 performs A/D-conversion on the received image signal.

The calculation control unit 14 includes a central processing unit (CPU), a read only memory (ROM), a hard disk (HDD), a random access memory (RAM), an interface circuit that performs transmission and reception of various signals with respective units which are electrically connected to each other, and the like. The calculation control unit 14 performs a variety of arithmetic processing according to various calculation control programs stored in the ROM, and also performs communication with the respective units to control the entire operation of the calculation unit 5.

The calculation control unit 14 is operated according to an inspection program 14a which is stored in the ROM or the HDD, analyzes the QR code 1a read by the reader 3 to acquire position data (absolute coordinates) on the pipe P, and associates the acquired position data on the pipe P with a flaw detection result obtained from the detection result according to the ultrasonic probe 2.

Next, configurations of the ultrasonic probe 2, the reader 3, an illumination 6, and the chassis 10 of the inspection system having such a configuration will be described in detail with reference to FIGS. 3 to 5. Here, a device configured by the ultrasonic probe 2, the reader 3, the illumination 6, and the chassis 10 is referred to as an inspection probe 100.

Figure 3:
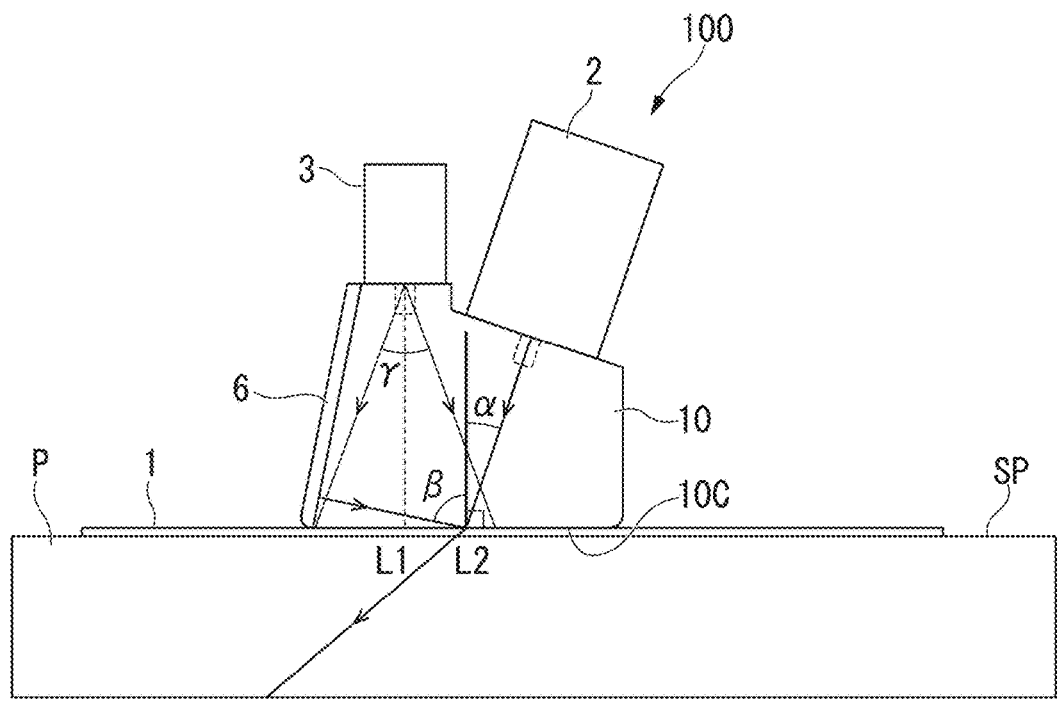
FIG. 3 is a side view of an inspection probe according to the first embodiment of the disclosure.

FIG. 3 is a side view of an inspection probe 100 according to the first embodiment of the disclosure. FIG. 4 is a plan view of the inspection probe 100 according to the first embodiment of the disclosure. FIG. 5 is a plan view of the chassis 10 according to the first embodiment of the disclosure.

The ultrasonic probe 2 of the inspection probe 100 shown in FIG. 3 is fixed to the chassis 10. Normally, the chassis 10 is integrally formed as a single member using a delay material having sonic wave permeability such as acryl. The chassis 10 of this embodiment is a member which is formed of a single acrylic resin which is formed in a solid shape and has an appearance such as a prism. Here, the delay material refers to a material that propagates an ultrasonic wave to a test object at an arbitrary angle by refracting the ultrasonic wave transmitted from the ultrasonic probe 2 like a lens.

In this embodiment, a method for fixing the ultrasonic probe 2 to the chassis 10 is screwing, but the ultrasonic probe 2 may be fixed to the chassis 10 using an adhesive. Further, the ultrasonic probe 2 and the chassis 10 may be formed as a chassis having an integral structure. Here, the material of the chassis 10 is not limited to acryl, and any material having transparency and sonic wave permeability may be used. In addition, the chassis 10 may be changed in shape according to a refraction angle of an ultrasonic wave used for inspection.

In addition to the ultrasonic probe 2, the reader 3 and the illumination 6 are fixed to the chassis 10. Accordingly, the chassis 10 functions as a delay member with respect to the ultrasonic probe 2, and functions as a prism with respect to the reader 3. That is, an ultrasonic wave and light are transmitted while being partially overlapped inside the chassis 10 which is the single acrylic resin as described later, and thus, miniaturization of the chassis 10 and the inspection probe 100 can be realized.

In this embodiment, a method for fixing the reader 3 and the illumination 6 to the chassis 10 is also screwing, but the fixing may be performed using an adhesive.

As shown in FIG. 3, in this embodiment, the reader 3 is fixed vertically downward to the chassis 10, and directly faces an opposing surface SP of a test object.

The ultrasonic probe 2 is fixed to the chassis 10 so that an incident point L2 where an ultrasonic wave transmitted from the ultrasonic probe 2 is incident onto the opposing surface SP of the test object is within an angle of view y of the reader 3 (so that the ultrasonic wave and light are transmitted while being partially overlapped inside the chassis 10). That is, the ultrasonic probe 2 is fixed to the chassis 10 at an acute angle α with respect to a line which is perpendicular to the opposing surface SP of the test object.

The ultrasonic wave transmitted from the ultrasonic probe 2 is incident onto the opposing surface SP of the test object at an incident angle α as shown in FIG. 3.

As shown in FIG. 3, the illumination 6 is fixed under the reader 3. Accordingly, illumination light emitted from the illumination 6 is incident onto the opposing surface SP of the test object at an incident angle β as shown in FIG. 3. It can be understood from FIG. 3 that the incident angle β of the illumination light is larger than the incident angle α of the ultrasonic wave. Therefore, the illumination 6 is fixed to the chassis 10 so that an incident angle β of illumination light that is incident onto the test object from the illumination is larger than an incident angle α of the ultrasonic wave that is incident onto the test object from the ultrasonic probe 2. Here, the incident angle α is preferably in a range from 5° to 35°, for example, and more preferably, in a range from 10° to 25°. In addition, the incident angle β is preferably in a range from 60° to 90° (excluding) 90°, and more preferably, in a range from 70° to 85°.

Furthermore, an arrangement position of the illumination 6 or the number thereof may be appropriately changed according to the shape of the chassis 10.

Figure 4:
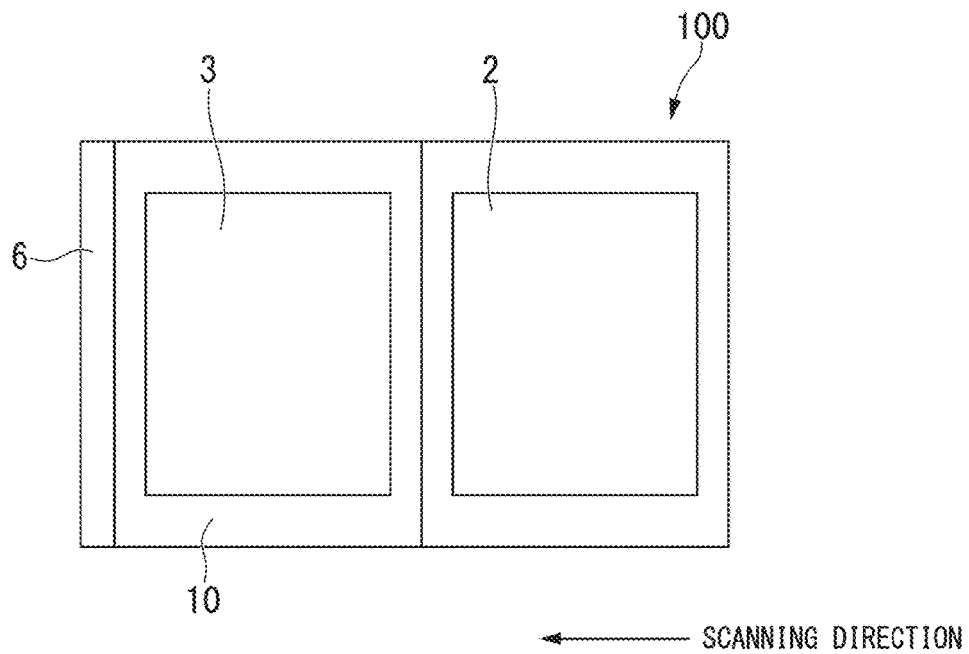
FIG. 4 is a plan view of the inspection probe according to the first embodiment of the disclosure.

A plan view of such an inspection probe 100 as seen from above is shown in FIG. 4. In this embodiment, the ultrasonic probe 2 is fixed on a rear side in a scanning direction of the inspection probe 100. However, the reader 3 may be fixed on the rear side in the scanning direction of the inspection probe 100, and the ultrasonic probe 2 may be fixed on a front side.

In this specification, for ease of description, a left direction on a paper plane of FIG. 4 is defined as the front side in the scanning direction of the inspection probe 100, but this is only an example, and the probe may be scanned in any direction in FIG. 4.

According to the inspection probe 100 of this embodiment described above, the following technical effects are achieved.

Since an acrylic resin having transparency and sonic wave permeability is used in the chassis 10, both of an ultrasonic wave input and output to and from the ultrasonic probe 2 fixed to the chassis 10 and light (image) input to the reader 3 fixed to the chassis 10 can pass through the chassis 10. Thus, it is possible to realize miniaturization of the chassis 10.

By realizing the miniaturization of the chassis 10, it is possible to realize miniaturization of the inspection probe 100 including the ultrasonic probe 2. Thus, operability of the inspection probe 100 is enhanced, and a range where scanning cannot be performed due to an obstacle is reduced.

Further, due to the miniaturization of the chassis 10, the distance between the reader 3 and the ultrasonic probe 2 is reduced. Thus, a distance between a view angle center position L1 of the reader 3 and the incident point L2 of the ultrasonic wave is reduced, and thus, the amount of position correction is reduced. Here, the position correction refers to correction performed to match, in a case where a position of absolute coordinates acquired from the QR code 1a read by the reader 3 and a position where a detection result of a test object detected by the ultrasonic probe 2 is obtained are different from each other although it is preferable that both the positions match each other, both the positions.

Further, according to the above-described embodiment, since the incident point L2 where an ultrasonic wave transmitted from the ultrasonic probe 2 is incident onto the opposing surface SP of the test object is within the angle of view y of the reader 3, it is possible to directly confirm a position where the ultrasonic wave is incident onto the test object in a captured image of the reader 3. Thus, it is possible to simultaneously confirm the presence or absence of insertion of air bubbles which is an obstacle of ultrasonic transmission and an ultrasonic waveform indicating the detection result of the ultrasonic probe 2 on the display unit 11 of the calculation unit 5, and thus, an inspector can focus on a flaw detection operation.

Figure 8A:
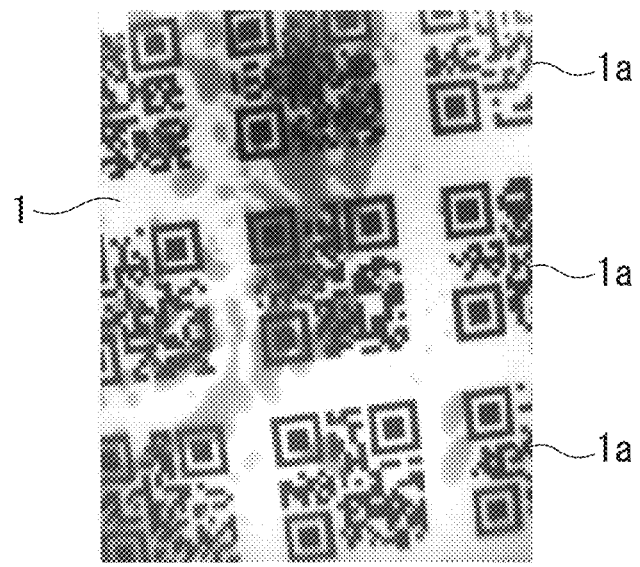
FIG. 8A is a diagram showing an example of reading an opposing surface of a test object using the inspection probe according to the first embodiment of the disclosure.
Figure 8B:
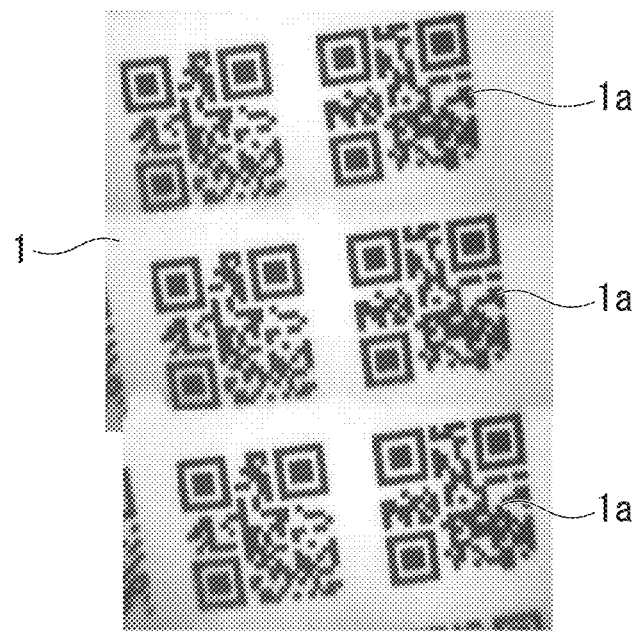
FIG. 8B is a diagram showing another example of reading the opposing surface of the test object using the inspection probe according to the first embodiment of the disclosure.

Reading examples of the presence or absence of such air bubble insertion are shown in FIGS. 8A and 8B. FIGS. 8A and 8B are both diagrams showing reading examples of an opposing surface SP of a test object using the inspection probe according to the first embodiment of the disclosure.

In FIG. 8A, a state where air bubbles are inserted in a contact medium applied under the sheet material 1 is shown. In this state, since an ultrasonic wave does not propagate in metal which is a test object, it is not possible to obtain an accurate detection result. On the other hand, in FIG. 8B, a state where insertion of air bubbles in a contact medium is not present and an accurate detection result can be obtained is shown.

Accordingly, according to this embodiment, an inspector can easily confirm the presence or absence of insertion of air bubbles, and can continuously perform inspection without noticing the insertion of air bubbles. As a result, it is possible to exclude a possibility that an accurate inspection result may not be obtained.

Further, the illumination 6 is fixed under the reader 3, and is fixed to the chassis 10 so as to be slightly inclined toward the opposing surface SP of the test object from the line which is perpendicular to the opposing surface SP of the test object. That is, the illumination 6 is fixed to the chassis 10 so that illumination light is incident onto the test object at the incident angle β. Thus, reading of the QR code 1a using the reader 3 is not hindered by illumination light reflected from the opposing surface SP of the test object, and thus, it is possible to accurately read position data of the opposing surface SP of the test object. The reason is as follows. That is, since illumination light has a large incident angle β with respect to the opposing surface SP of the test object due to such an installation angle of the illumination 6 with respect to the chassis 10, it is considered that illumination light that is emitted from the illumination 6 and is reflected from the opposing surface SP of the test object without being incident onto the test object and reflected light of illumination light that is incident onto the test object are not incident onto the reader 3. That is, the illumination 6 is fixed to the chassis so that illumination light that is emitted from the illumination 6 and is reflected from the opposing surface SP of the test object without being incident onto the test object and reflected light of the illumination light that is incident onto the test object are not incident onto the reader 3.

If the above-described inclined angle of the illumination 6 is represented using the incident angle β of the illumination light, it can be said that the illumination 6 is provided to be inclined with respect to the line which is perpendicular to the opposing surface SP of the test object by an angle (90−β)°. Accordingly, in consideration of the above-described range of the incident angle β, the illumination 6 is preferably inclined with respect to the line which is perpendicular to the opposing surface SP of the test object in a range from 0° to 30° (excluding) 0°), for example, and more preferably, in a range from 5° to 20°.

Figure 5:
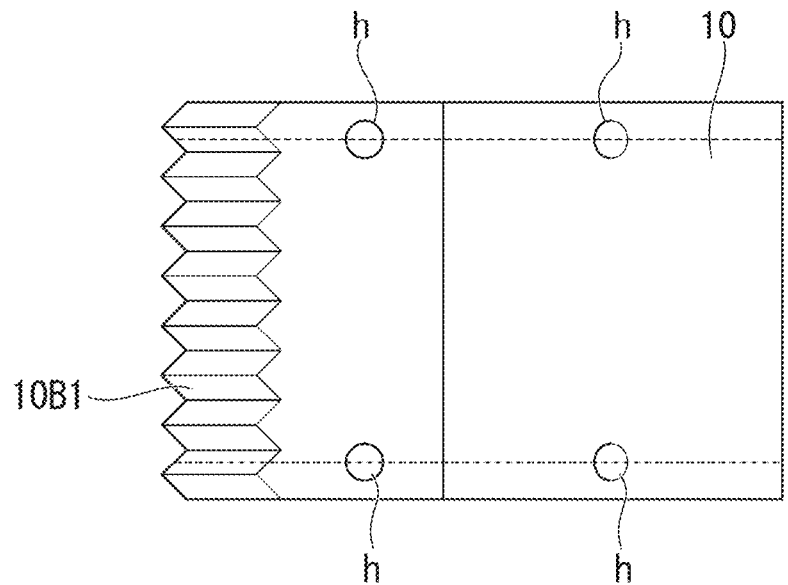
FIG. 5 is a plan view of a chassis according to the first embodiment of the disclosure.

An end surface 10B1 of the chassis 10 of this embodiment on a side where the illumination 6 is fixed is formed in a shape having a saw blade section as shown in FIG. 5. This shape is formed to perform diffused reflection with respect to reflected waves that are incident onto the end surface 10B1, among reflected waves of ultrasonic waves that are transmitted from the ultrasonic probe 2 and are incident onto a test object, or reflected waves of ultrasonic waves that are reflected from the test object without being incident onto the test object, to thereby prevent an influence on detection of reflected waves of ultrasonic waves that are directly incident onto the ultrasonic probe 2.

Here, hole portions at four places shown in FIG. 5 represent screw holes h where screws are inserted when the ultrasonic probe 2 and the reader 3 are fixed to the chassis 10.

Further, an antireflection film may be attached to a surface of the chassis 10, or the surface of the chassis 10 may be coated with black paint. This is performed to prevent sunlight from being incident onto the chassis 10 during operation outdoors, and to prevent external light such as illumination from being incident onto the chassis 10 during operation indoors.

In addition, as shown in FIG. 3, the chassis 10 is formed so that sharpness of opposite end portions of a surface 10C of the chassis 10 that faces the opposing surface SP of the test object is removed. This is formed to cause the chassis 10 to be able to smoothly move on the opposing surface SP of the test object.

Further, in a case where the test object is a pipe, the surface 10C of the chassis 10 that faces the opposing surface SP of the test object (pipe) may be processed in a concave shape to match a curved surface of the pipe.

Next, a first modification example of the first embodiment of the disclosure will be described with reference to FIG. 6A.

In the following description, points different from those of the first embodiment will be described, and the same reference signs are given to the same components as those of the first embodiment, and description thereof will not be repeated.

Figure 6A:
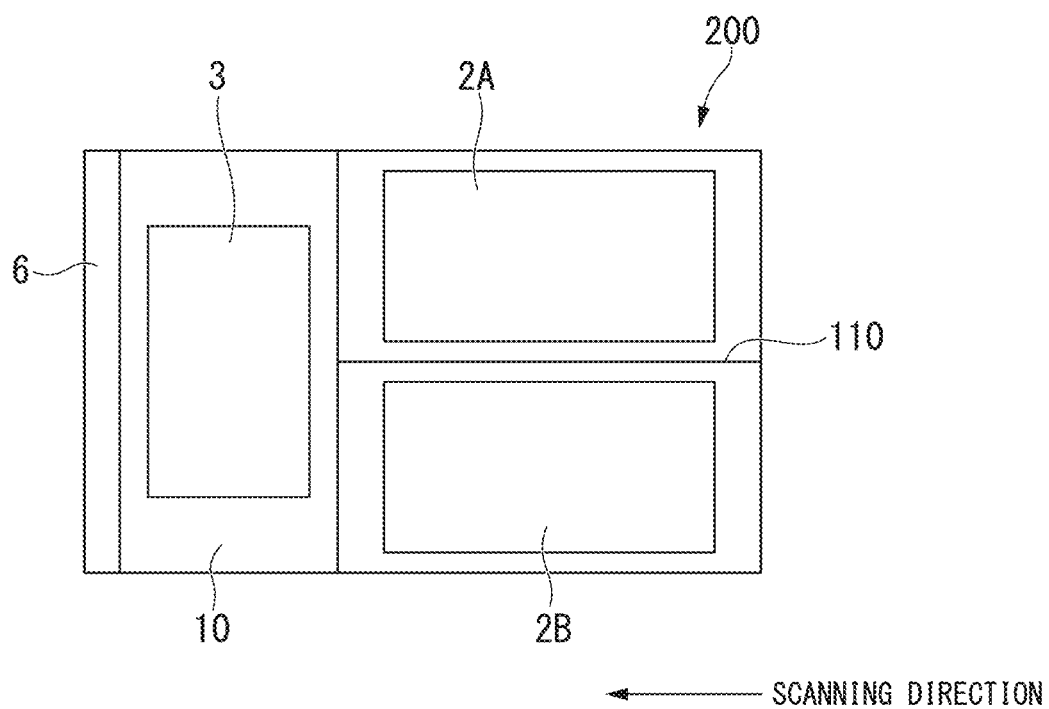
FIG. 6A is a plan view of an inspection probe according to a first modification example of the first embodiment of the disclosure.

FIG. 6A is a plan view of an inspection probe 200 according to the first modification example of the first embodiment of the disclosure.

In the first modification example of the first embodiment of the disclosure, as shown in FIG. 6A, the ultrasonic probe 2 of the first embodiment includes a transmission ultrasonic probe 2A and a reception ultrasonic probe 2B. Here, the transmission ultrasonic probe 2A and the reception ultrasonic probe 2B are separated acoustically by an acoustical separator for double crystal probe 110. Further, the reader 3 is fixed in an approximately central portion of the chassis 10 when dividing the chassis 10 into upper and lower halves on a paper plane of FIG. 6A.

Here, the acoustical separator for double crystal probe 110 is present only on a side where scanning of the inspection probe 200 is advanced in a scanning direction with reference to the reader 3 as shown in FIG. 6A, but may extend up to the vicinity of the illumination 6 although not shown. In a case where the acoustical separator for double crystal probe 110 extends up to the vicinity of the illumination 6, the reader 3 is disposed so as not to interfere with the acoustical separator for double crystal probe 110.

According to the inspection probe 200 that includes the transmission ultrasonic probe 2A and the reception ultrasonic probe 2B having such a configuration, similarly, it is possible to achieve the same technical effects as those of the inspection probe 100 that includes the ultrasonic probe 2 of the first embodiment.

Figure 6B:
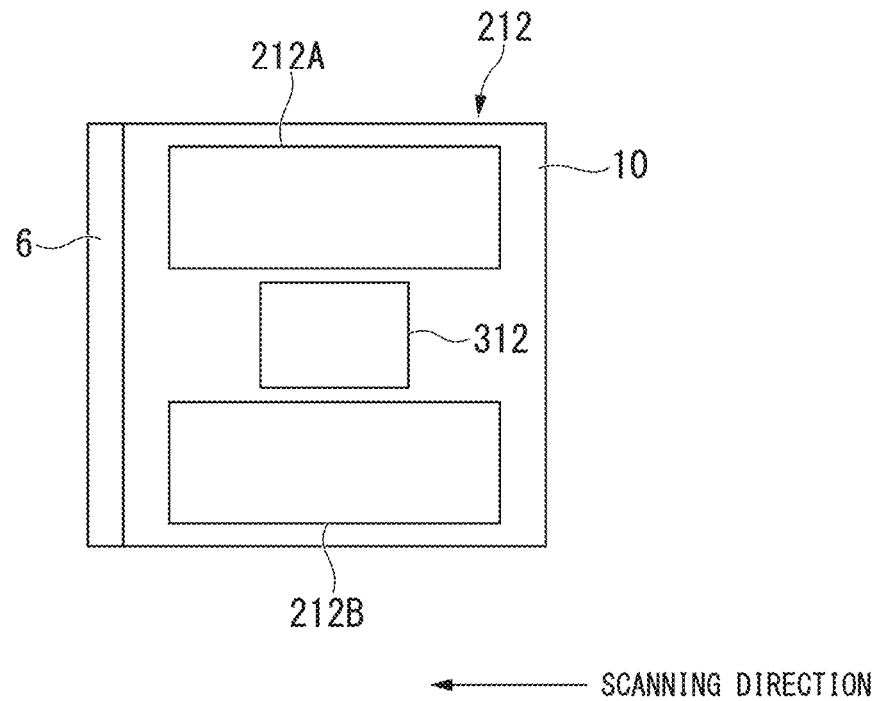
FIG. 6B is a plan view of an inspection probe according to a second modification example of the first embodiment of the disclosure.

In a case where acoustic inference does not affect inspection, the acoustical separator for double crystal probe 110 may not be provided. For example, as an example in which the acoustical separator for double crystal probe 110 is not provided, there is a second modification example of the first embodiment, as shown in FIG. 6B. FIG. 6B is a plan view of an inspection probe 212 according to a second modification example of the first embodiment of the disclosure. In the following description using FIG. 6B, the same reference signs are given to the same configurations as those of the first modification example of the first embodiment of the disclosure as shown in FIG. 6A, and a description thereof will not be repeated.

In the second modification example of the first embodiment of the disclosure shown in FIG. 6B, a reader 312 is provided between a transmission ultrasonic probe 212A and a reception ultrasonic probe 212B. According to the inspection probe 212 having such a configuration, similarly, it is possible to achieve the same technical effects as those of the inspection probe 100 that includes the ultrasonic probe 2 of the first embodiment.

Figure 7:
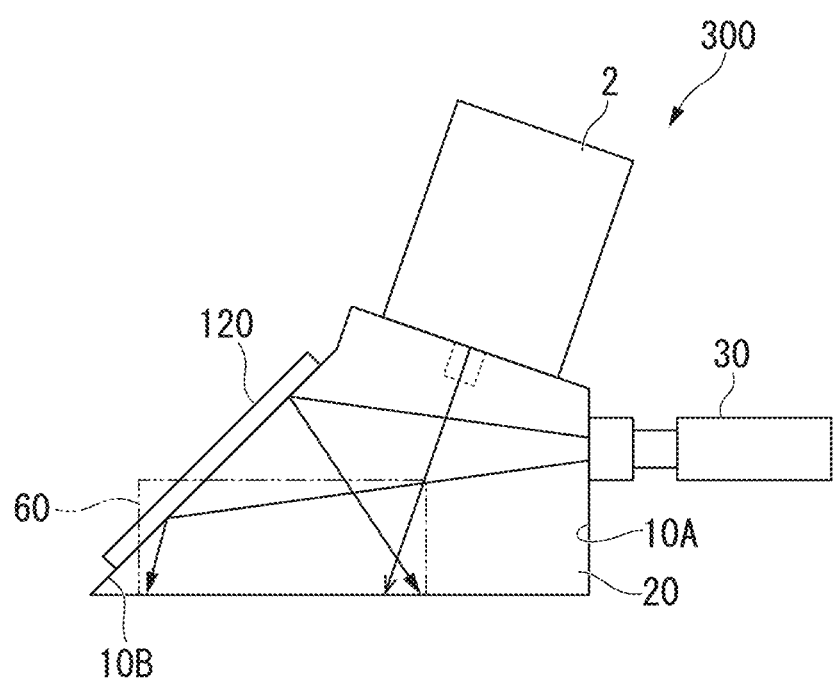
FIG. 7 is a side view of an inspection probe according to a third modification example of the first embodiment of the disclosure.

Next, a third modification example of the first embodiment of the disclosure will be described with reference to FIG. 7. FIG. 7 is a side view of an inspection probe 300 according to a third modification example of the first embodiment of the disclosure.

In the third modification example of the first embodiment shown in FIG. 7, a reader 30 is fixed to an end surface 10A of a chassis 20. As shown in FIG. 7, the end surface 10A is formed to be approximately perpendicular to an opposing surface SP of a test object, and the reader 30 is fixed to the end surface 10A to be approximately perpendicular thereto.

Here, the "approximately perpendicular" refers to a range including "perpendicular" and about 10° on both sides of "perpendicular" to be considered "perpendicular".

Further, on an end surface 10B of the chassis 20 on a side opposite to the side where the reader 30 is fixed, a mirror 120 is fixed, and the reader 30 reads a QR code 1a that is reflected on the mirror 120. For this reason, when viewing the mirror 120 from the reader 30, the mirror 120 is fixed along the end surface 10B inclined with respect to the opposing surface SP of the test object so that the QR code 1a is reflected on the mirror 120.

Further, illuminations 60 are fixed to both surfaces of the chassis 20 which perpendicularly intersect a scanning direction of the inspection probe 300.

According to the inspection probe 300 having such a configuration, similarly, it is possible to achieve the same technical effects as those of the inspection probe 100 that includes the ultrasonic probe 2 of the first embodiment. Further, according to the above-described third modification example of the first embodiment, the end surface 10B to which the mirror 120 is fixed is inclined with respect to the opposing surface SP of the test object at an acute angle. Thus, the inspection probe 300 according to the third modification example of the first embodiment may be used for a test object having an obstacle for which the inspection probe 100 shown in the first embodiment cannot be used.

Hereinbefore, the embodiments of the disclosure have been described, but a technical scope of the disclosure is not limited to the embodiments, and may additionally include various modifications in a range without departing from the concept of the disclosure.

For example, the chassis has a rectangular shape in a planar view in the above-described examples, but as long as mutual position relationships between the ultrasonic probe 2, the reader 3 or 30, the illumination 6 or 60, and the mirror 120 as described in the embodiment are satisfied, an outer shape of the chassis may be a rounded shape, or may be an arbitrary shape familiar with hands of an inspector. For example, the chassis 10 may have a shape like a mouse.

Further, the illumination may not be fixed to the entirety of a surface of the chassis, but instead, may be appropriately disposed to be fitted for the shape of the chassis 10. Furthermore, a plurality of illuminations may be provided.

The disclosure is used for internal inspection of a test object using an ultrasonic probe, but may also be used for surface inspection of a test object.

Further, a pipe is used as an example of a test object, but the test object is not limited to the pipe.

In the above description, there is a case where the sonic wave is written instead of the ultrasonic wave, but this is because only the ultrasonic wave is not emitted from the ultrasonic probe but the sonic wave may also be emitted therefrom.

Further, in the above description, an incident point where an ultrasonic wave transmitted from the ultrasonic probe 2 is incident onto the opposing surface SP of the test object is represented as L2, and L2 is shown in FIG. 3. Further, in the above description, the ultrasonic wave transmitted from the ultrasonic probe 2 is incident onto the opposing surface SP of the test object at the incident angle α shown in FIG. 3, and illumination light emitted from the illumination 6 is incident onto the opposing surface SP of the test object at the incident angle shown in FIG. 3. However, in FIG. 3, it seems that L2 is not an incident point with respect to the opposing surface SP of the test object but is an incident point with respect to the sheet material 1, and that α and β are not incident angles with respect to the opposing surface SP of the test object but are incident angles with respect to the sheet material 1. However, these are shown like that for ease of illustration. Accordingly, as described herein, an incident point where an ultrasonic wave transmitted from the ultrasonic probe 2 is incident onto the opposing surface SP of the test object is L2, the ultrasonic wave transmitted from the ultrasonic probe 2 is incident onto the opposing surface SP of the test object at the incident angle α shown in FIG. 3, and illumination light emitted from the illumination 6 is incident onto the opposing surface SP of the test object at the incident angle β shown in FIG. 3.

According to the disclosure, it is possible to prevent reading of a pattern using an optical sensor from being hindered by reflected light from an opposing surface of a test object. Further, it is possible to easily confirm whether air bubbles are inserted between the pattern on the opposing surface of the test object and the optical sensor. Thus, it is possible to accurately read the pattern on the opposing surface of the test object, and thus, it is possible to prevent the pattern from being continuously read although sonic waves are not incident due to insertion of air bubbles.

While preferred embodiments of the disclosure have been described and shown above, it should be understood that these are exemplary of the disclosure and are not to be considered as limiting. Additions, omissions, substitutions, and other modifications can be made without departing from the spirit or scope of the present disclosure. Accordingly, the disclosure is not to be considered as being limited by the foregoing description, and is only limited by the scope of the appended claims.

What is claimed is:

1. An inspection system comprising:
   a sheet material which is disposed on a test object and on which a two-dimensional pattern indicating a position on the test object is drawn; and
   an inspection probe that includes:
      a chassis that is freely movable on the sheet material and has transparency and sonic wave permeability;
      an ultrasonic probe that is freely movable on the test object and irradiates the test object with an ultrasonic wave to detect a reflected wave, and is fixed to the chassis;
      a reader that is fixed to the chassis and reads the two-dimensional pattern, the reader having a predetermined angle of view; and
      an illumination that is fixed to the chassis; and
   a calculation unit that executes arithmetic processing according to a detection result according to the ultrasonic probe to acquire a flaw detection result of the test object,
   wherein the ultrasonic probe is fixed to the chassis such that an incident point of an ultrasonic wave that is incident onto an opposing surface of the test object from the ultrasonic probe is within the angle of view of the reader.

2. The inspection system according to claim 1, wherein the illumination is fixed to the chassis such that an incident angle of illumination light that is incident onto the test object from the illumination is larger than an incident angle of the ultrasonic wave that is incident onto the test object from the ultrasonic probe.

3. The inspection system according to claim 1, wherein the illumination is fixed to the chassis such that illumination light that is emitted from the illumination and is reflected from the opposing surface of the test object without being incident onto the test object and reflected light of the illumination light that is incident onto the test object are not incident onto the reader.

4. The inspection system according to claim 1, wherein the illumination is fixed under the reader.

5. The inspection system according to claim 1, wherein the chassis is formed of a single solid acrylic resin.

* * * * *